United States Patent [19]

Hanson

[11] Patent Number: 5,648,603
[45] Date of Patent: Jul. 15, 1997

[54] METHOD AND APPARATUS FOR STABILIZING A QUANTITATIVE MEASUREMENT GAS TRAP USED IN A DRILLING OPERATION

[75] Inventor: Scott Alan Hanson, Houston, Tex.

[73] Assignee: Texaco Inc., White Plains, N.Y.

[21] Appl. No.: 566,805

[22] Filed: Dec. 4, 1995

[51] Int. Cl.$^6$ .............................. E21B 49/00; G01N 1/00
[52] U.S. Cl. ............................................ 73/152.02; 73/863
[58] Field of Search .......................... 73/152.02, 152.15, 73/152.12, 152.46, 863, 23.22, 23.2, 53.01, 53.07

[56] References Cited

U.S. PATENT DOCUMENTS

| | | | |
|---|---|---|---|
| 3,050,449 | 8/1962 | Moore | 204/152 |
| 4,687,523 | 8/1987 | Hall et al. | 73/863 |
| 4,848,487 | 7/1989 | Anderson et al. | 175/58 |
| 5,199,509 | 4/1993 | Write et al. | 73/153 |
| 5,310,282 | 5/1994 | Voskamp | 405/58 |
| 5,334,239 | 8/1994 | Choe et al. | 95/261 |

*Primary Examiner*—Richard Chilcot
*Assistant Examiner*—Max H. Noori
*Attorney, Agent, or Firm*—Henry H. Gibson; William J. Beard

[57] ABSTRACT

Methods and apparatus for improving the quantitative measurement and detection of gas entrapped in drilling fluid during a drilling operation are disclosed. A sealed gas sampler is provided for agitating the mud to evolve gas samples. A known quantity of a standard gas is injected into the evolved gas stream. By monitoring the quantitative amount of the standard gas measured, the samples of evolved gas may be corrected for various error sources such as gas saturation of the sample stream.

8 Claims, 2 Drawing Sheets

METHOD AND APPARATUS FOR STABILIZING A QUANTITATIVE MEASUREMENT GAS TRAP USED IN A DRILLING OPERATION

BACKGROUND OF THE INVENTION

The present invention relates to the quantitative measurement of gas entrapped in drilling fluids during the drilling operation in an oil well. More particularly, this invention relates to improved methods and apparatus for performing quantitative measurements of such entrapped drilling mud gas using gas trap sampling systems such as that of U.S. Pat. No. 5,199,509 which is assigned to the assignee of the present invention.

Drilling mud is pumped down the drill string in a rotary drilling operation. It serves multiple purposes. It cools and lubricates the drill bit at the end of the drill string. It balances pressure between the earth formations and the borehole. It carries "cuttings" of drilled rock to the surface and it collects and entraps fluid samples from penetrated earth formations of oil, gas and water. Drilling muds are typically comprised of solids entrained in a water based or oil based slurry of weighting fluids such as barite or the like.

Mud logging is the term which has been applied to the surface monitoring of the entrapped fluids and gasses in the drilling mud when it is circulated to the surface during a drilling operation. In order to extract and measure light hydrocarbon gasses from the return flow of drilling mud, samples of the mud are collected in a gas trap.

The purpose of the gas trap is to quantitatively measure the amount of gas in the drilling fluid. This measurement has presented a problem with prior art gas traps because of air and gas leaks through the fluid exhaust port, which is generally open to the air outside the trap, and leakage around the stirrer bar motor shaft, the stirrer being used to agitate the drilling fluid inside the gas trap so that it will release entrapped formation gasses.

The aforementioned U.S. Pat. No. 5,199,509 describes an improved gas trap system which overcomes some of the measurement problems by provision of a discrete air vent line whose far end is in gas-free air and by reducing or eliminating uncontrolled gas phase mixing at the mud exit port and from the agitator shaft seal leaks. However even this system is improved upon further by use of the methods and apparatus of the present invention.

In order for a gas measurement system to be quantitative, gas separated from the drilling fluid by the gas trap must be drawn through a sample line at a known flow rate. The gas is then measured using a gas chromatograph and a total hydrocarbon analyzer. Gas-in-air measurements of the gas from the gas trap can then be related back to actual gas-in-mud levels. Periodic gas-in-mud measurements must be made in order to "calibrate" a quantitative gas trap. This calibration can consist of collecting a known volume of drilling fluid at the gas trap and then distilling that sample in a Steam Still such as that of U.S. Pat. No. 3,050,449 which is incorporated herein by reference. The distilled gas is then measured and compared with gas measurements direct from the trap to determine what the relative recovery is from the gas trap for each gas component of interest.

In order for a gas measurement system to remain stable enough to relate gas-in-air to gas-in-mud certain parameters of the gas trap need to be monitored. These are:
1) The flow rate of the sample being pulled from the gas trap should be known and remain constant;
2) the speed of the gas trap agitator should be known and remain constant;
3) The gas trap must be sealed against wind effect to prevent uncontrolled sample dilution;
4) Gas evolved from the drilling fluid should not exceed the sample rate which would cause gas trap saturation; and
5) The gas trap should not be sensitive to mud level changes caused by gas trap immersion variations.

Sealed gas traps can saturate at high gas-in-mud levels when total gas evolution rate exceeds the trap sample flow rate. The agitation action of the gas trap can create bubbles in the drilling fluid entering the trap. Such bubbles can recapture and carry off some of the gas evolved from the sample. Traps equipped with air powered motors can develop leaks in the bearings of the motor shaft allowing air to enter directly from the motor shaft into the sealed gas trap. This can dilute the gas sample at unknown rate.

BRIEF DESCRIPTION OF THE INVENTION

The methods and apparatus of the present invention approach the solution of several of the problems of sealed gas traps from a different angle. Gas trap saturation and leaks in a sealed system are overcome by injecting a "standard" gas or known gas directly into the gas trap body at a known flow rate.

The problem of gas trap saturation is rendered recognizable by this approach, and the trap maintained quantitative, even when saturated and losing gas out the vent because the amount of gas lost is known due to the measured loss of the injected "standard" gas. Also the injection of the standard gas directly into the gas trap provides a quality of measurement check. The sample rate of the standard gas dilution can be monitored by measuring the dilution of the standard gas (from its known quantitative value) at the gas chromatograph. Such a check is independent of drilling operations because the standard gas injected directly into the gas trap does not mix with the drilling fluid. Thus if there are leaks in the sealed gas trap, the vacuum line pulling the sample into the trap or in the air motor bearings, such will appear as lower standard gas readings.

The standard gas chosen for injection into the gas trap may be any gas not found in the earth formation being drilled or in the atmosphere. Typical examples of standard gasses which have been used successfully for this purpose comprise, Ethylene, Isobutylene or Nitrous Oxide ($N_2O$). Other gasses than these could be used, if desired, so long as these do not cause measurement ambiguities.

The invention will be best understood by reference to the following detailed description thereof, when taken in conjunction with the accompanying drawings. The description and drawings are intended as illustrative only and not as limitative of the invention. In the accompanying drawings:

DETAILED DESCRIPTION OF THE INVENTION

Figure 1:
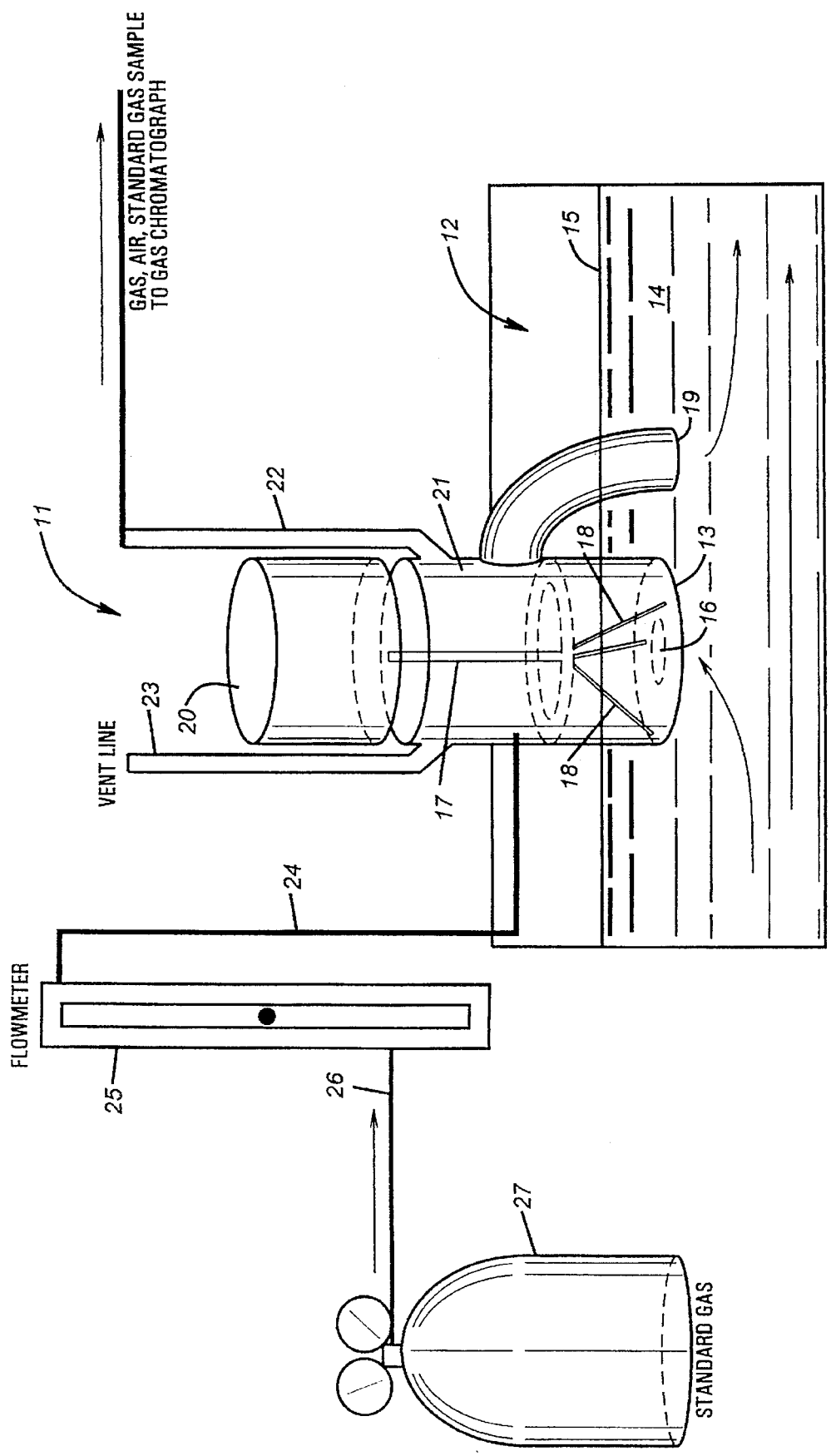
FIG. 1 is a schematic representation showing a mud logging system employing concepts of the invention deployed in a mud pit during a drilling operation.

Referring initially to FIG. 1, the gas trap system of the present invention is shown schematically deployed in a drilling mud tank 12 during a rotary drilling operation. The gas trap shown generally at 11 is vertically mounted in the drilling mud pit 12 such that its lower end 13 is always below the surface 15 of drilling mud 14 flowing (as arrows indicate) in the pit or tank 12. The gas trap unit 11 is preferably of the type shown and described in U.S. Pat. No. 5,199,509 which is assigned to the assignee of the present invention and which is incorporated herein by reference for all purposes. Other types of sealed gas traps could be used if desired, without compromising the inventive concepts of the present invention. Drilling fluid or mud 14 is drawn into the housing of gas trap 11 through its lower entry orifice 16. After processing as will be described in more detail, the mud is returned below the surface 15 via mud exit port 19.

Mud 14 entering trap 11 is drawn in to the apparatus 11 by a slightly lower pressure maintained in the head space 21 by a vacuum or pump rate in sample line 22. Sample line 22 evacuates evolved mud gasses and standard gas to a gas chromatograph (not shown) for quantitative measurement. An air vent line 23 also enters the head space 21 and allows the vacuum rate or suction rate in line 22 to be set to any desired value, regardless of gas devolution rates inside the sample chamber of apparatus 11.

Upon entry into gas trap 11 the drilling mud 14 is subjected to vigorous agitation by agitator blades 18 driven by shaft 17 and powered by an air motor 20. This agitation evolves entrapped gasses in the mud which rise to enter head space 21 of the gas trap. Also entering the head space 21 of the trap 11 is a standard gas from a standard gas source 27, depicted schematically in FIG. 1 as a pressurized tank. Standard gas supply 27 supplies the standard gas via a flow meter 25 and line 26 to the standard gas input line 24 which enters head space 21 via a standard fitting (not shown). The flow meter 25 is a calibrated flow meter and is used to assure a known flow rate (which is held constant) for standard gas injection. With the vacuum system on (line 22) and the agitator 17, 18 off, injection of standard gas is begun. The percent by volume of the standard gas is then read at the output of the gas chromatograph (not shown). After the standard gas reading is stabilized and established, the gas trap 11 agitator 17, 18 is turned on. The stabilized measured amount of standard gas detected at the chromatograph will not change until the gas trap becomes saturated.

A portion of the measured amount of injected standard gas will drop in a saturated trap as some of this gas in the head space 21 will be carried out the mud exit port 19 in the form of bubbles entrapped in the drilling mud 14. This sample loss due to bubbles caused by mud agitation can be monitored for changes which occur if the drilling fluid properties change.

It has been observed that the standard gas selected should not be naturally occurring in the atmosphere, the earth formations, nor should it be easily soluble in water. When oil based muds are used in drilling the gas should not be soluble in oil. In runs made with Nitrous Oxide as the standard gas it was observed that $N_2O$ was easily soluble in the water based mud drilling fluid but not in oil based muds. While the $N_2O$ runs were successful, it has been found that Ethylene or Isobutylene are less soluble in water and work better as a standard gas for injection in water based muds.

Figure 2:
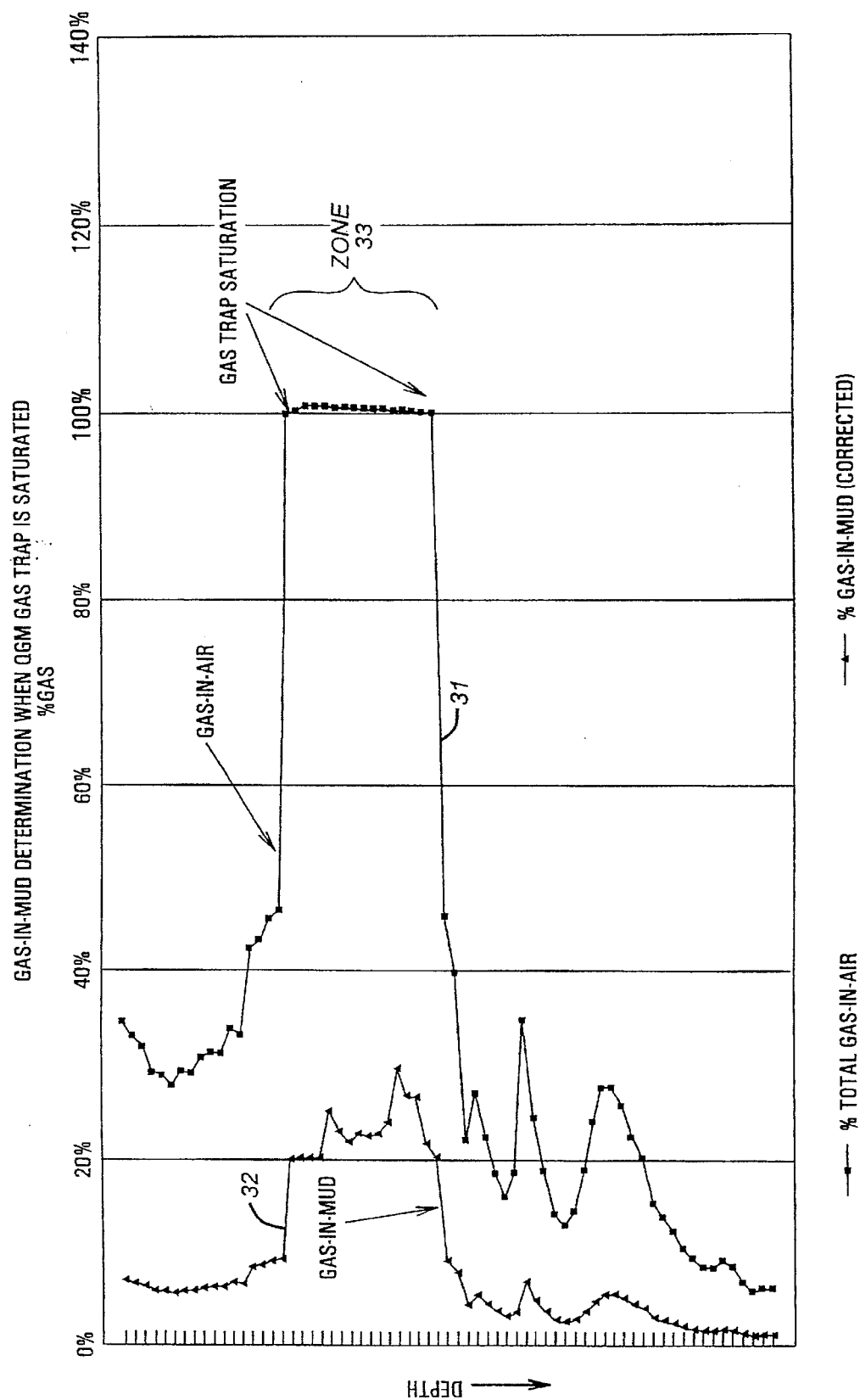
FIG. 2 is a graphical representation illustrating use of concepts of the present invention in compensating for gas saturation in a mud logging gas trap.

Referring now to FIG. 2, a graphical representation is shown illustrating how the injection of the standard gas can overcome the loss of quantitative measure caused by saturation of the head space 21 of the gas trap 11 by particularly gassy muds. In FIG. 2 the vertical scale is depth and the horizontal scale is percent gas both in mud (curve 32) and in air (curve 31). A particularly gassy zone 33 causes the saturation of the gas trap and curve 31 "flat tops" because of this. However curve 32, which is the gas in mud curve which is corrected for saturation by the addition of the portion of the known standard gas quantity percentage lost to saturation, correctly shows the percent gas in mud in spite of the gas in air curve saturation. By comparing the standard gas percentage reading before, during, and after the "flat topped" gas in air zone 33, it is possible to deduce the portion of that percentage lost to saturation. This amount is then added in to the gas in mud percentage over the "flat topped" zone 33 to get the corrected gas-in-mud curve 32 over this zone. Thus it is seen how the injection of a known or marker standard gas can be used to correct what would otherwise be erroneous saturated readings.

In summary, a standard gas is injected into the gas trap at a known constant rate prior to agitation and used to establish a reference baseline in the output of the gas chromatograph. Agitation is then begun and the known baseline is corrected for the amount of standard gas lost due to bubbles caused by agitation. This corrected standard gas baseline may then be used to determine (due to baseline shifts) if standard gas is being lost due to saturation of the sample line to the gas chromatograph. If it is, then the known percentage lost of the sample gas can be added in to correct the lost evolved gas lost through saturation.

The foregoing descriptions may make changes and modifications of the inventions apparent to those of skill in the art. It is the aim of the appended claims to cover all such changes and modifications that fall within the true spirit of the invention.

I claim:

1. In a mud logging system an improved gas trap comprising:

a generally cylindrical housing having a restricted opening bottom end, a closed top end and a restricted opening intermediate member, said intermediate member having at least four ports;

means for mounting said housing member in a flowing mud receptacle with said housing in a substantially vertical position with said bottom end of said housing extending below the top surface of flowing mud in said receptacle;

motor driven agitator means for agitating mud drawn from said receptacle into said housing to evolve gasses trapped therein into said restricted opening intermediate member;

mud exhaust port means from said restricted opening intermediate member to return mud below the top surface of the mud in said receptacle;

vent line means for admitting substantial gas free air to said intermediate member via a vent pod in said intermediate member;

means for injecting a constant known percentage of standard gas into said restricted opening intermediate member via a standard gas port in said intermediate member; and means to draw off gas, including said standard gas, from said restricted opening intermediate member via a sample gas port in said intermediate member to a quantitative gas measurement system.

2. The system of claim 1 wherein said means for injecting a constant known percentage of standard gas includes a pressurized source of said standard gas.

3. The system of claim 2 wherein said means for injecting further includes a quantitatively calibrated flow meter between said gas source and said restricted opening intermediate member and flow lines connecting said source, said flow meter and said restricted opening intermediate member.

4. A method for correcting gas saturated samples of trapped gas in a drilling mud receptacle during a mud logging operation comprising the steps of:

a) sampling drilling mud entrapped gas and air at a constant rate during mud logging operation;

b) injecting a known percent by volume of a standard gas into said sampled drilling mud entrapped gas and air;

c) quantitatively measuring the percent by volume of entrapped gas, standard gas and air in said sampled drilling mud entrapped gas and air;

d) determining any variation in the known injection percentage of said standard gas and the standard gas detected in step c); and e) correcting the measured percentage of entrapped gas as a function of the difference of the known and the measured percentages of standard gas to provide a corrected output of percentage of entrapped gas.

5. The method of claim 4 wherein the step of injecting a standard gas is performed by injecting a gas not found naturally in the atmosphere or in the earth formation being drilled.

6. The method of claim 5 wherein the step of injecting a standard gas is performed by injecting ethylene gas.

7. The method of claim 5 wherein the steps of injecting a standard gas is performed by injecting isobutylene gas.

8. The method of claim 5 wherein the step of injecting a standard gas is performed by injecting a gas not readily soluble in water.

* * * * *